United States Patent [19]  [11] 4,055,177
Cohen  [45] Oct. 25, 1977

[54] HYPODERMIC SYRINGE

[76] Inventor: Milton J. Cohen, 9201 Persimmon Tree Road, Potomac, Md. 20854

[21] Appl. No.: 690,846

[22] Filed: May 28, 1976

[51] Int. Cl.² ............................................. A61M 5/00
[52] U.S. Cl. ............................................. 128/218 M
[58] Field of Search ...... 128/218 M, 218 D, 218 DA, 128/218 R, 218 N, 218 NV, 215, 216, 220, 221, 234, 272.3, 272

[56] References Cited

U.S. PATENT DOCUMENTS

| 1,557,836 | 10/1925 | Hein | 128/220 |
| 2,159,217 | 5/1939 | Lozier et al. | 128/218 M |
| 2,460,039 | 1/1949 | Scherer et al. | 128/218 NV |
| 3,489,147 | 1/1970 | Shaw | 128/218 M |
| 3,636,950 | 1/1972 | Gomez et al. | 128/218 M |
| 3,684,136 | 8/1972 | Baumann | 128/218 M X |
| 3,785,379 | 1/1974 | Cohen | 128/218 M |

Primary Examiner—John D. Yasko
Attorney, Agent, or Firm—McDougall, Hersh & Scott

[57] ABSTRACT

A hypodermic syringe formed of a single tubular member which is subdivided into chambers by a sealing member intermediate the ends of the tubular member and which includes a penetrating needle mounted in axial alignment with the sealing member in position to penetrate the sealing member responsive to axial displacement thereof to establish communication between the chambers for flow of material from one chamber to the other for admixture immediately prior to injection.

7 Claims, 4 Drawing Figures

HYPODERMIC SYRINGE

This invention relates to a device for injection of a liquid in the form of a solution or dispersion, wherein two of the components are maintained in a separated relation until just prior to injection.

The invention has to do with materials, such as medicaments, which cannot be premixed without deterioration, loss of activity or the like, and therefore are required to be mixed in measured amounts only immediately prior to use, as by injection. The invention is restricted to a mixture of two or more materials, at least one of which is in a liquid state, while the other or others can be in the form of powder, liquid or particulate form for solution or suspension in the liquid phase.

In my previously issued U.S. Pat. No. 3,785,379, description is made of a syringe suitable for use in the injection of materials of the type described, which are maintained in measured amounts in a separated relation, and admixed one with the other immediately prior to use. In the aforementioned patent, use is made of a syringe formed of one vial telescoped within another, in which the solid or liquid component to be admixed with the liquid phase is contained in the one vial, while the liquid phase to be combined with the solid or liquid is contained in another vial which is telescoped into the first. The one vial is sealed at one end by a rupturable membrane and a hollow needle is supported in position to rupture the sealing membrane when the mixed materials are ready for injection.

The telescoping end portion of the other vial is provided with a sealing ring that extends into sealing engagement with the inner walls of the telescoped vial to enable the telescoping vial to move axially within the telescoped vial as a piston. A free floating disc member extends in sealing engagement with the interior walls of the other vial to retain the liquid phase therein and a hollow needle is secured in the telescoping end portion of the other vial in position to pierce the disc member responsive to displacement of the disc member into engagement therewith and thereby to provide a passage through which the liquid phase can flow from the other vial into the first vial for admixture with the material therein.

A piston is located within and in sealing engagement with the inner walls of the other vial, in spaced relation with the sealing disc, to confine the liquid phase therebetween. The piston member is provided with means for actuation to displace the piston plug axially in the other vial.

In operation, responsive to displacement of the piston in the direction towards the telescoping end portion of the vial, pressure is imposed on the confined liquid phase to actuate the disc member to move axially in the direction toward the hollow needle. In response to continued pressure, the needle pierces the disc member and the liquid phase is forced from the other vial, through the hollow needle and into the first vial for admixture with material contained therein. Upon transfer of the measured amount of liquid phase from the other vial, the unit is shaken to effect mixture of the material for uniform dispersion of solution. Thereafter, the hypodermic needle is released to pierce the sealing disc on the end of the first vial to enable the mixed materials to be displaced from the vial, and through the hypodermic needle in response to pressure applied as the telescoping vial is actuated as a piston for axial movement through the first vial.

It is an object of this invention markedly to simplify the construction and operation of a device of the type described, including a material reduction in the elements of which it is formed, with corresponding reduction in cost, all without change in the mode of operation or utility.

These and other objects and advantages of this invention will hereinafter appear and for purposes of illustration, but not of limitation, an embodiment of the invention is shown in the accompanying drawings in which FIG. 1 is a schematic sectional elevational view of a device embodying the features of this invention with the elements in loaded position;

Figures 1, 2, 3, 4:
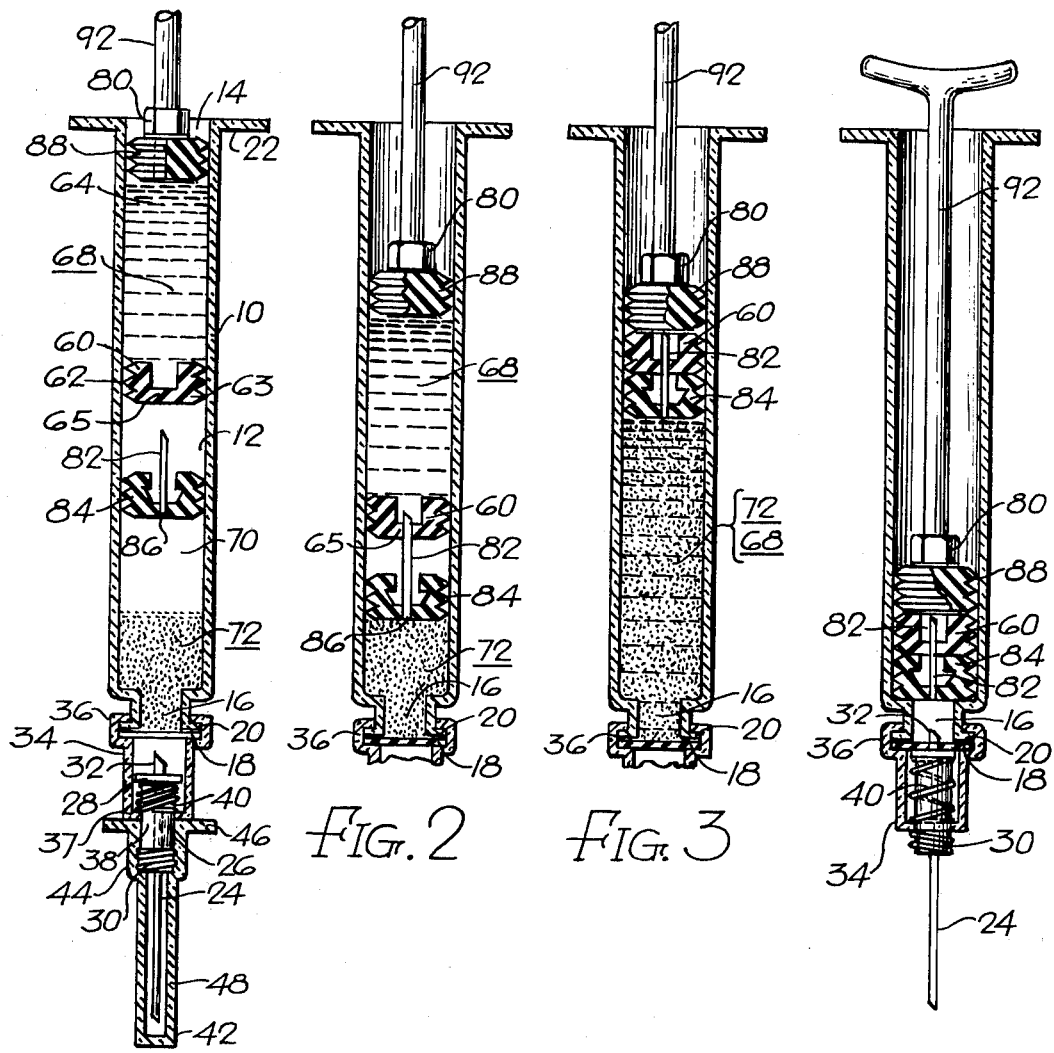
FIG. 2 is a sectional view similar to that of FIG. 1 showing the arrangement of elements responsive to the initial axial displacement of the piston plug.
FIG. 3 is a sectional view similar to those of FIGS. 1 and 2 showing the arrangement of elements after the piston plug has been actuated to displace the liquid phase.
FIG. 4 is a sectional view similar to those of FIGS. 1-3 in which the piston plug has been actuated to effect displacement of the mixed materials from the device.

In accordance with the practice of this invention, the second vial which is telescoped for operation as a piston through the first vial and which houses the liquid phase, is completely eliminated. Instead, use is made of but a single elongate tubular member or vial 10 formed of glass, plastics, or the like material having a bore 12 extending continuously therethrough from an open rearward end 14 to a forward open ended neck portion 16. The forward open end is adapted to be sealed by means of a rupturable sealing disc member 18 dimensioned to span the opening 16 and to abut the outwardly extending annular lip 20 on the end of the neck portion 16. The rearward end of the vial is formed with an outwardly extending flanged portion 22 which serves as a finger grip for purposes which will hereinafter be described.

The hypodermic needle 24 is mounted in a needle hub 26, in the form of a cylindrical member having an outwardly extending flanged portion 28 at its rearward end and a threaded portion 30 in the peripheral surface at the forward end.

Means are provided to secure the sealing disc member 18 in sealing relation onto the open end of the vial 10 and to mount the needle hub 26 for axial displacement in the direction toward and away from the vial 10, with the rearward end 32 of the needle in endwise alignment with the sealing disc 18, and spaced a short distance forwardly thereof, when in normal retracted position, and to pierce the disc member 18 and extend into the interior of the vial 10 when in operated position. Such means is illustrated as comprising a cup member 34 having a rearward end portion 36 which is clamped about the outwardly extending lip 20 with the sealing disc 18 therebetween securely to position the disc 18 in sealing relation across the open end of the vial. The body portion of the cup member 34, having a diameter greater than the flanged portion 28, extends forwardly for a distance and is thereafter formed with an inwardly turned portion 37 to define an opening 38 corresponding to the cross-sectional dimension of the needle hub to enable the latter to slide axially therein. The needle hub 26 and the supported needle 24 are continuously urged towards operated position by means of a compression spring, in the form of a coil spring 40 which surrounds the needle hub, with one end abutting the shelf 37 while the other end abuts the annular flange 28 on the rearward end of the needle hub.

The needle hub is held in its normally retracted position with the rearward end 32 of the needle 24 positioned immediately in advance of the sealing disc 18, as by means of a needle cover 42 having a cupped rearward end portion 44 dimensioned to correspond with the cross-section of the needle hub, and a flanged portion 46 extending outwardly from the rearward end thereof. The needle cover comprises a tubular portion 48 dimensioned to receive the end portion of the needle 24. The internal wall of the cupped portion 44 is threaded for threaded engagement with the forward end portion of the needle hub whereby the needle cover is threaded onto the threaded end portion of the needle hub by an amount to bring the inturned portion 37 into engagement with the flanged portion 46 whereby the needle hub is retained in retracted position with the rearward end of the needle spaced a short distance forwardly of the sealing disc and with the compression spring 40 in a tensioned relation such that, when the cover is removed, the needle hub is released for axial displacement by the tensioned spring. Thus the needle hub is displaced automatically rearwardly to project the end of the needle 24 through the sealing disc 18 and into the interior of the vial 10.

In accordance with the practice of this invention, the need for a second vial mounted in telescoping relation with the first vial and in sealing engagement therewith is completely eliminated with corresponding simplification in the construction of the device and use, and with corresponding reduction in cost of the device and ease in operation.

This can be achieved, in accordance with the practice of this invention, by the construction wherein use is made of a sealing disc 60 dimensioned to correspond with the internal diameter of the bore 12 with the peripheral portion 62 of the sealing disc in sliding engagement with the inner wall of the vial to subdivide the vial into a rearward portion 64, in which the liquid phase 68 is retained, and a forward portion 70, in which the liquid or solid phase 72 is retained for admixture with the liquid phase.

The sealing disc 60 of rubber, plastic or the like material is preferably formed with one or more axially spaced peripheral ribbed portions 63 for more effective sealing engagement with the inner wall of the vial. For purposes which will hereinafter be described, the inner portion 65 of the sealing disc 60 is formed to lesser thickness than the outer portion to maximize the sealing engagement with the walls of the vial while minimizing the thickness of the material to be pierced for communicating the interior of the section 64 with the section 70.

For the latter purpose, there is provided, in the forward portion 72, a means for supporting a hollow needle 82 with the pointed end of the needle extending rearwardly in axial alignment to pierce the reduced portion 65 of the sealing disc 60 responsive to forward displacement of the disc member into engagement with the needle whereby communication is established through the needle between the two axially aligned sections. This enables liquid phase to flow from the rearward section 64 through the needle into the forward section 70. The needle is supported by a disc member 84 of rubber, plastics, metal or the like material, with the periphery of the disc member 84 in sealing engagement with the inner wall of the vial 10 and with a passage 86 through the central portion of the disc member into which the hollow needle extends. Both of the disc members 84 and 60 are mounted for free sliding axial movement within the vial.

The rearward end of the vial 10 is sealed with a rubber plug 88 mounted for axial displacement through the bore 12, in the manner of a piston plug. Means, such as a threaded stud 90, is provided on the rearward end of the plug 88 for connection of an actuator rod 92 for displacement of the piston plug through the bore 12.

In use, the liquid or powdered material 72 is loaded into the forward section 70. The needle disc 84 is mounted in the space above the material and the sealing disc 60 is positioned in the vial immediately beyond the end of the needle 82. Thereafter the liquid phase is confined in the space 64 between the sealing disc 60 and the piston plug 88, as illustrated in FIG. 1.

In this arrangement, the measured amount of the two materials to be mixed is provided in a single vial for storage and/or shipment, with the materials in their separated sealed compartments.

When it is desired to inject a mixture of the measured amounts of the two materials, the actuator 92 is screwed onto the piston plug 88.

With one hand, the unit is grasped with the fingers beneath the finger flanges 22 and the palm of the hand over the actuator in position axially to displace the actuator in response to hand pressure. As the piston plug 88 is displaced in the vial in the forward direction, movement is transmitted through the confined liquid phase 68 to the sealing disc 60 whereby continued axial displacement will cause the sealing disc to be displaced into engagement with the pointed end of the hollow needle 82.

The needle 82 will pierce the sealing disc whereby communication as illustrated in FIG. 2 is established between the liquid 68 in the rearward section 64 and the space 70 in which the material 72 is located to enable the liquid phase to be forced from the rearward section 64, through the needle 82 into the space 70 in response to continued actuation of the piston plug. Instead of piercing the sealing disc 60, the liquid phase, sealing disc 60 and needle holder 84 may be displaced forwardly as a column until the holder comes into engagement with the material 72 confined in the forward section thereafter to resist further axial displacement, at which time the continued movement of the piston plug and disc member will cause the pointed end of the needle 82 to pierce the plug for the described communication. In the latter instance, as the liquid phase is forced from the rearward section 64 into the forward section 70, the holder 84 and sealing disc 60 will be axially displaced rearwardly by the increasing volume of liquid forced into the forward chamber, as illustrated in FIG. 3.

When the liquid phase has been displaced into the forward chamber, the unit is shaken to combine the materials in solution or dispersion, after which the materials are ready for injection.

Thereafter the needle cover 42 is removed to expose the needle 24 and free the compression spring 40 for rearward displacement of the needle hub 26 whereby the rearward end portion 32 of the needle 24 is projected through the sealing disc 18 into communication with the interior of the chamber 70 containing the mixture of materials.

Administration is made without change of device and without exposure of the freshly prepared solution or suspension by inserting the needle 24 into the vessel or disc. The piston plug is again displaced axially forwardly after the needle has been inserted to cause displacement of the piston plug through the vial forcibly to displace the freshly prepared mixture from the interior of the chamber, through the needle and into the disc, as illustrated in FIG. 4.

I claim:

1. In a hypodermic syringe for injection of a liquid composition formulated of at least two ingredients, one of which is a liquid phase, to be maintained in a separated relation until admixture with the other ingredients immediately prior to injection, comprising a single unitary elongate tubular member having a bore extending continuously therethrough from an open forward end to an open rearward end of the tubular member, a rupturable sealing disc mounted on the forward end of the tubular member to seal the open forward end, a piston plug within the tubular member dimensioned to extend crosswise of the bore into sealing engagement with the inner walls of the tubular member for axial sliding movement relative thereto as a piston and means for actuating said piston plug for axial movement within the bore, a rupturable sealing member axially slidable within the tubular member and extending crosswise of the bore into sealing engagement with the internal walls of the tubular member between the sealing disc and the piston plug to subdivide the bore of the tubular member into forward and rearward chambers separated in sealing relation by the sealing member for receipt of the liquid phase material in the rearward chamber and the other ingredient in the forward chamber, a disc member adjacent the rupturable sealing member dimensioned to extend crosswise of the bore into sealing engagement with the inner walls of the tubular member for axial sliding movement relative thereto, and a hollow penetrating needle fixed to said disc member to provide a passage therethrough with the end of the needle extending axially beyond the disc member in the direction towards the sealing member whereby the needle penetrates the sealing member responsive to axial movement to bring the needle into engagement to penetrate the sealing member to enable the liquid phase to flow from the rearward chamber into the forward chamber responsive to axial displacement of the piston plug forwardly in the bore.

2. A hypodermic syringe as claimed in claim 1 which includes a hypodermic needle mounted on the forward end portion of the tubular member in position to pierce the sealing disc.

3. A hypodermic needle as claimed in claim 1 in which the bore is of uniform diameter substantially throughout the length of the tubular member.

4. A hyperdermic syringe as claimed in claim 1 in which the sealing member subdividing the bore into forward and rearward chambers comprises a disc member having spaced axially spaced ribs in the periphery for sealing engagement with the walls of the tubular member.

5. A hypodermic syringe as claimed in claim 4 in which the sealing member is formed of an elastomeric material.

6. A hypodermic syringe as claimed in claim 1 in which the sealing member is formed with an outer peripheral portion of greater thickness than the central portion to define a central well into which the end of the needle extends upon penetration of the sealing member.

7. A hypodermic syringe as claimed in claim 1 in which the sealing disc on the end of the tubular member is formed of an elastomeric material.

* * * * *